United States Patent [19]

Hubbard et al.

[11] Patent Number: 4,776,343
[45] Date of Patent: Oct. 11, 1988

[54] DISPOSABLE PRESSURE TRANSDUCER FOR USE WITH A CATHETER

[75] Inventors: James R. Hubbard, Moorestown, N.J.; Geoffrey B. Boulden, Lockport; David M. DiSabito, Clarence, both of N.Y.; Joseph Pelensky, Philadelphia, Pa.

[73] Assignee: Graphic Controls Corporation, Buffalo, N.Y.

[21] Appl. No.: 916,520

[22] Filed: Oct. 8, 1986

Related U.S. Application Data

[63] Continuation-in-part of Ser. No. 799,408, Nov. 19, 1985, abandoned.

[51] Int. Cl.⁴ .............................................. A61B 5/02
[52] U.S. Cl. .................................... 128/675; 128/673; 73/708
[58] Field of Search ................................ 128/672–673, 128/675, 748; 73/706, 708, 715, 756; 339/28, 36, 40, 44 R, 176 MP; 439/528, 136, 142

[56] References Cited

U.S. PATENT DOCUMENTS

| | | | |
|---|---|---|---|
| 3,863,504 | 2/1975 | Borsanyi | 128/672 X |
| 4,197,959 | 4/1980 | Kramer | 339/44 R X |
| 4,227,420 | 10/1980 | Lamadrid | 73/756 |
| 4,237,935 | 12/1980 | Delmonte et al. | 128/675 X |
| 4,252,126 | 2/1981 | Mandl | 128/675 X |
| 4,291,702 | 9/1981 | Cole et al. | 128/675 |
| 4,431,009 | 2/1984 | Marino, Jr. et al. | 128/675 X |
| 4,514,032 | 4/1985 | Lawrence | 339/176 MP X |
| 4,539,998 | 9/1985 | McCord et al. | 128/675 |
| 4,545,389 | 10/1985 | Schaberg et al. | 128/675 X |
| 4,576,181 | 3/1986 | Wallace et al. | 128/675 |

FOREIGN PATENT DOCUMENTS

| | | | |
|---|---|---|---|
| 1116997 | 6/1968 | United Kingdom | 128/673 |
| 2117190 | 10/1983 | United Kingdom | 339/36 |

Primary Examiner—Kyle L. Howell
Assistant Examiner—Angela D. Sykes
Attorney, Agent, or Firm—Ratner & Prestia

[57] ABSTRACT

A disposable blood pressure transducer system for use with a catheter with or without a catheter flush/flow valve. The transducer housing has both electrical and fluid connections, with the electrical connections being protected from contamination by fluid.

7 Claims, 5 Drawing Sheets

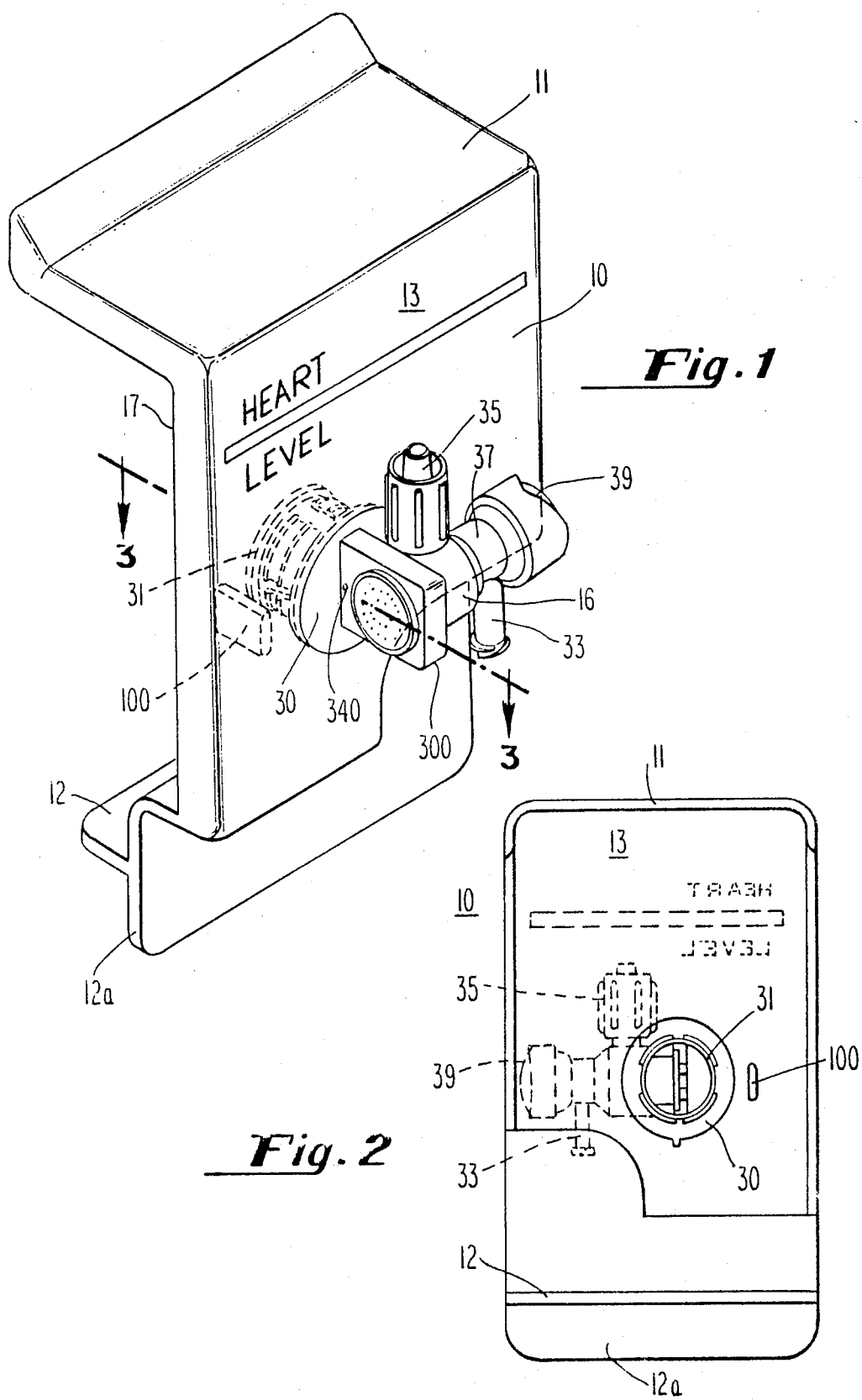

DISPOSABLE PRESSURE TRANSDUCER FOR USE WITH A CATHETER

RELATED APPLICATION

This application is a continuation-in-part of application Ser. No. 799,408 filed Nov. 19, 1985, now abandoned.

BACKGROUND OF THE INVENTION

Accurate and continuous measurement of blood pressure requires catheterization of the blood vessel of interest. Typically, the tip of a thin hollow catheter is inserted into the blood vessel to the point of interest. Saline solution is then typically infused through this catheter in order to provide a medium for the transmission of pressure waves through the catheter to a transducer element located outside the body.

Traditionally, pressure transducers have been reusable elements involving some sort of strain-sensitive resistive wires or semiconductor elements bonded to a diaphram which contacts the pressure transmitting fluid. However, such reusable pressure transducers introduce the possibility, over time, of contamination and deterioration of the delicate transducer elements. Repeated sterilizations, daily wear and tear such as temperature variation, pressure variation, impact, and vibration, may all contribute to reduced sensitivity, linearity, accuracy, and life of such a reusable device.

In order to overcome the deficiencies of reusable pressure transducers, there have been developed disposable pressure transducers. Such disposable transducers have several advantages over the reusable type including the necessity to sterilize each unit only once, the reduction in handling, wear and tear, the avoidance of environmental variations in repetitive usage, and the enhanced electrical characteristics of a single use element solid state transducer.

Among the disposable blood pressure transducing elements commercially available are those manufactured by Cobe Laboratories, Inc., Gould, Inc., Norton Company, Sorensen Research Company, and Healthdine Cardiovascular, Inc.

Of the commercially available models, all are generally used by mounting on a bedside vertical pole directly below a saline source, typically a sterile plastic bag. Fluid connections are typically made with Linden fittings which are either molded as part of the device housing or attached to short lengths of plastic tubing. Alternatively, fluid connections may be made with Luer-lock fittings and some units may be mounted on the upper arm of the patient by using a strap and special mounting base.

Most commercially available disposable pressure transducers are connected to their associated monitoring electronics through an attached short length of electrical wire terminating in a connector. This wire is generally refered to as a "pigtail."

Because pressure transducers are typically mounted on a bedside pole directly below a saline source, isolation of electrical connections from the saline solution is especially important. A shortcoming of those units lacking a pigtail connection is their susceptibility to damage from saline exposure, either during installation, or during operation due to leaking connections. Such damage may not be externally evident to the attending professionals but rather may affect the accuracy and reliability of the transducer elements, thereby exposing the patient to unnecessary risk. In those units having a pigtail, electrical connections may be made to the unit after its installation on the pole. However, such units are often equally susceptible to leaking connections since fluid can travel down the pigtail and invade the connector.

Typically, these disposable transducers are associated with, and in some cases are made integral with a catheter patency flush/flow valve assembly and housing, through which saline solution is infused through an indwelling vascular catheter at a selectively controlled rate.

It is the general objective of the present invention to provide a disposable pressure transducer system, for continuous blood pressure monitoring, which is less susceptible (than those heretofore available) to fluid contamination of electrical connections.

BRIEF DESCRIPTION OF THE INVENTION

A catheter-type pressure transducer system, constructed in accordance with the present invention, has two main components: a housing in which the pressure transducer is located and a cable having a connector for receiving the transducer signal and conducting the signal to a remote blood pressure indicating instrument. The housing has first and second fluid ports, a fluid flow path between the fluid ports, and an electrical connection port electrically isolated from the fluid flow path. Pressure transducer means are positioned in pressure sensing communication with the fluid flow path for developing a signal representative of the pressure of a fluid in the fluid flow path. Electrical connecting means extending from the pressure transducer means into the electrical connection port bring the transducer signal to the cable connector. The body of the cable connector engages the electrical connection port with a fluid seal. In a preferred embodiment of the invention, the housing is mounted on a splash curtain with the entrances to the fluid ports on one side of the curtain and the entrance to the electrical connection port on an opposite side of the curtain. Preferably also, the transducer assembly and housing are made integral with a catheter patentcy flush/flow valve assembly and housing (sometimes referred to as a "catheter flush/flow valve").

BRIEF DESCRIPTION OF THE FIGURES

FIG. 1 is a perspective view of a first embodiment of the present invention.

FIG. 2 is a rear view of the FIG. 1 embodiment of the present invention.

DETAILED DESCRIPTION OF THE INVENTION

Figure 3:
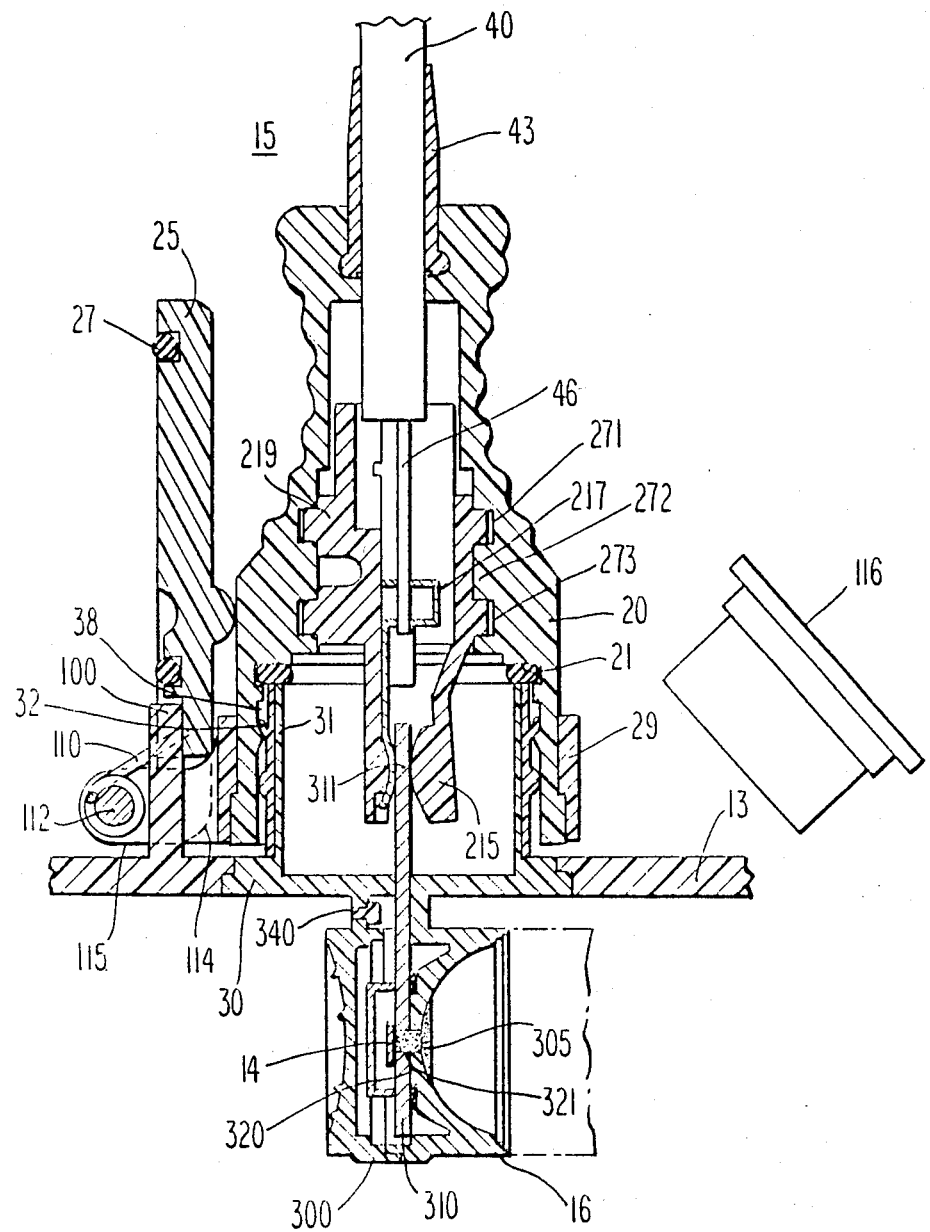
FIG. 3 is a partial cross-sectional view taken along line 3—3 of FIG. 1 with an associated cable and plug.

Referring now to FIGS. 1 and 2, there is shown a pressure transducer system catheter flush/flow valve assembly constructed in accordance with the present invention. In operation, the entire assembly depicted in FIGS. 1 and 2 would be clamped to a pole and held securely in place by a separate gripping member clamped about a flange 12 on the backside of splash curtain 10 or about flange 12a on the bottom of curtain 10. Curtain 10 carries catheter flush/flow valve housing 16 having fluid inlet port 33, fluid outlet port 35, an internal fluid flow path between inlet port 33 and outlet port 35, and electrical connection port 31 isolated from the fluid flow path.

A source of saline solution usually mounted above the transducer/flusher on a vertical pole or optionally including an infusion pump mounted remotely is connected to fluid inlet port 33 and flows in either a slow flow mode or a flushing mode through the flusher and exits at fluid outlet port 35 which is connected to a catheter. The position of a manual actuator 39 of a valve, at a location in the valve housing identified by reference numeral 37, regulates the flow rate of fluid flowing from fluid inlet port 33 to fluid outlet port 35. Actuator 39 is springbiased into a position permitting only slow fluid flow. By pushing actuator 39 inward (to the right in FIG. 2), the valve opens to permit a faster flushing flow.

At the leftward end (as shown in the figures) of housing 16 is transducer housing 300 in which is located a pressure transducer means (not shown in FIG. 1) positioned in the fluid flow path between fluid inlet port 33 and fluid outlet port 35. The pressure transducer means and its operation will be considered in greater detail in connection with FIG. 3.

Curtain 10 comprises front surface 13, top flange 11, a pair of side flanges 17 (only one is shown in FIG. 1) and curtain mounting flanges 12 and 12a. As will be appreciated from the figures, curtain 10 is designed to deflect fluid impinging upon it from the top or front away from its rear surface at which electrical connection port 31 opens. Shielding of electrical connection port 31 from fluid which drops from a saline solution bag or connecting tubes is accomplished by mounting housing 16 on splash curtain 10 with the openings to fluid ports 33 and 35 on one side of the curtain and the opening to electrical connection port 31 on an opposite side of the curtain.

Referring now to FIG. 3, one sees, in section, the left hand end of housing 16, transducer housing 300 and pressure transducer means as described more fully below. A cable 40 conducts the transducer signal to a remote blood pressure indicating instrument. Housing 300 is sealingly secured (such as by a sealing adhesive) to splash curtain 10 by means of a mounting flange 30 which is a part of housing 300 and fits within a corresponding opening in the curtain, so that electrical connection port 31 protrudes from the back surface of curtain 10.

Within transducer housing 300, transducer 14 is mounted on transducer circuit card 310. Card 310 includes associated equalization circuitry necessary for operation of the transducer and slide-on connector leads (not shown) at the end 311 of card 310 distal from transducer 14.

Circuit card 310 is adhesively bonded to leftwardly facing inner surface 320 of housing 300. Surface 320 includes pressure transmitting port 321, by which transducer element 14 is coupled, for pressure sensing, to the fluid flowing from inlet port 33 to outlet port 35. Pressure transmitting cylindrical plug 305 (a silicone gel in this embodiment of the invention), sealingly disposed in port 321, effects electrical isolation of electrical connection port 31 from the fluid flow path in housing 16, while effecting a pressure sensing (or transmitting) communication between transducer 14 and that fluid path. Plug 305 is suitably opaque to reduce light-sensitive effects present in the transducer. Transducer 14, in this embodiment of the invention, comprises a micromachined silicon diaphragm device in which electrical characteristics change in response to changes in the pressure in the medium being sensed and with which the device is in physical contact.

Electrical connection port 31 is in the form of a barrel-shaped socket. End 311 of circuit card 310 extends into this socket and presents sliding contact points (not shown) which are engaged when a mating cable connector 15 at the end of cable 40 is fitted over the socket. Connector 15 has a cylindrical recess within its body 20 which is tightly fitted over the outside surface of socket 31. Located at the rear end of the cylindrical recess is an O-ring 21 which is engaged by the edge of socket 31 and prevents fluid entry into the interior of the cable connector when it is secured in position on socket 31. A detent ring 32 on socket 31 engages a groove 38 in cable connector 15 as the connector is fitted over the socket. This engagement maintains the relationship between the connector and the socket and thereby controls the sealing compression of O-ring 21. At its distal end, cable 40 transmits the transducer signal to a remote blood pressure indicating instrument.

Within connector body 20 is housed a pair of floating connector members 219 and 215 which cooperate to create a reliable electrical connection between the sliding contact points of circuit card 310 and the wires in cable 40. Connector body 20 is entered at its rear-most end by cable 40 which is provided with a water-tight elastomeric seal and strain relief means 43. The conductors within cable 40 are separated into a plurality of wires of which wire 46 is but one. These wires are attached to a plurality of electrical contact members of which 217 is but one. Electrical contact member 217 is carried upon connector member 219 and is opposed by connector member 215. Both connector member 215 and connector member 219 are carried within a pair of mating recesses 271 and 273 formed by a flange 272 of connector housing 20. It should be noted that connector members 219 and 215 are allowed a small degree of freedom to move within connector body 20 and thus adjust to imperfections and variations of position of circuit card 310.

When connector 15 is attached to socket 31, air is trapped within the connector, the socket and housing 300 containing transducer 14, thereby creating a pressurized environment. Unless vented, such a pressurized environment would provide an incorrect indication of pressure. Housing 300, in the vicinity of transducer 14, therefore, has a vent port filled with a vent plug 340 which is composed of a porous hydrophobic material. Vent plug 340 permits pressure equilibration with atmospheric pressure n order to assure accurate readings while preventing the entry of aqueous fluids into the vicinity of the transducer or its associated electronics and connectors.

Cable connector 15 carries a protective cap 25 which provides further protection against entry of fluid into the interior of the connector. Cap 25 is mounted on connector 15 for pivotal movement between an open position, as shown in FIG. 3, and a closed position in which the cylindrical recess within the connector body is closed by the cap. Cap 25 pivots about the axis of a pin 112 which passes through a pair of spaced extensions 114 on the cap (only one is shown in FIG. 3) and a pair of spaced supports 115 on the connector (only one is shown in FIG. 3). A spring 110 biases cap 25 to cover the cylindrical recess within the connector body when the connector is disconnected from socket 31. While the connector is connected to socket 31, protective cap 25 is retained in its open position by a retaining post 100 which extends away from the rear surface of curtain 10 and engages the cap. Upon removal of connector 15 and disengagement of cap 25 from post 100, spring 110 urges the cap to move to the closed position (counter-clockwise in FIG. 3) and seal off the opening into the recess in the connector. This is accomplished by an O-ring 27 which is carried by the cap as the O-ring is compressed against the open end of connector body 20. When cable connector 15 is being connected to socket 31, protective cap 25 is retracted against the action of spring 110 and held in place by the user's thumb until the desired connection is made and post 100 engages the cap.

Figure 4:
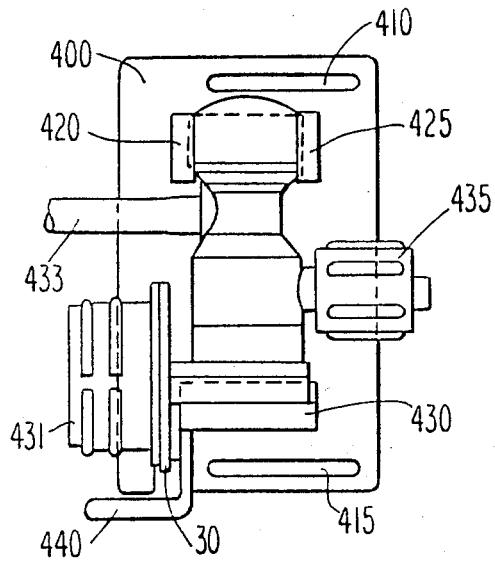
FIG. 4 is a front view of a second embodiment of the present invention.
Figure 5:
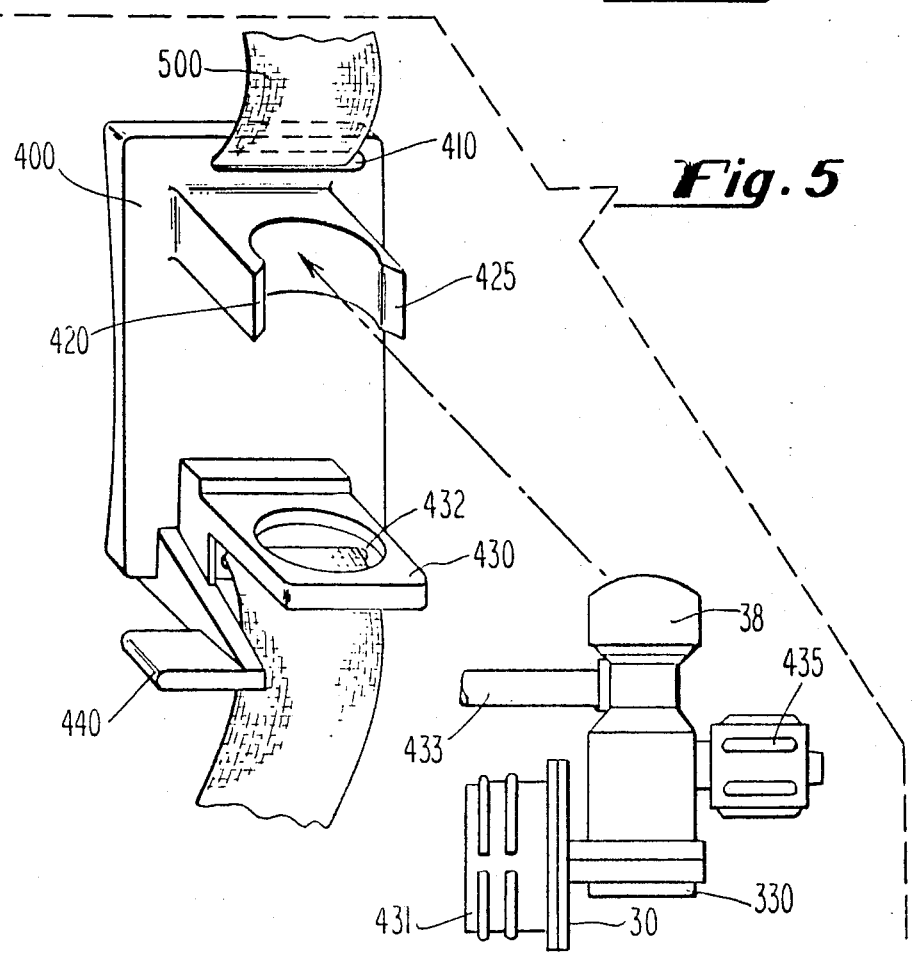
FIG. 5 is an exploded perspective view of the FIG. 4 embodiment of the present invention.

For further protection against entry of fluid into the interior of socket 31, the transducer/flusher unit is supplied with a disposable elastomeric cap 116. Cap 116 is removed from socket 31, as shown in FIG. 3, so that cable connector 15 can be connected to socket 31. -5 Referring now to FIGS. 4 and 5, there is shown an alternative mounting for the transducer/flusher of the present invention. As depicted in FIGS. 4 and 5, curtain 10 of FIG. 1 is replaced by a mounting base 400. The entire transducer/flusher assembly is removably mounted on base 400 which is then secured in position directly on the patient being monitored. Typically, base 400 is secured by a strap having an opposing hook and loop closure (e.g. "VELCRO") means 500 which is passed continuously through a pair of slots 410 and 415 in base 400. The entire transducer/ flusher assembly is retained in place on base 400 by its insertion into a mounting plate 430 which has a central opening 432 for receiving a cylindrical projection 330. In addition, a pair of opposing jaws 420 and 425 resiliently retain a flange 38 surrounding actuator 39.

It should be noted that in this patient mounted configuration, the relative orientations between electrical socket 431 and fluid outlet port 435, as depicted in FIG. 4, are different from the relative orientations of electrical socket 31 and fluid outlet port 35, as depicted in FIG. 1. In FIG. 1, socket 31 and outlet port 35 are at a right angle to one another, while in FIG. 4 the two extend parallel to one another in opposite directions. In addition, luer fitting 33 of the pole mounted version of Figure 1 is replaced by a short length of hollow tubing 433 which may terminate in a luer fitting. Tubing 443 may be of such a length as to displace its fluid connection from the region of flange 30. Alternatively, tubing 433 may be flexible to allow it to be displaced out of the region of flange 30. Finally, cap retaining post 100 of the pole mount version is present as post 440 of the patient mounted version.

In all other respects, the patient mounted version of the present invention is identical to the pole mounted version and contains elements as depicted in FIGS. 1–3.

Figure 6:
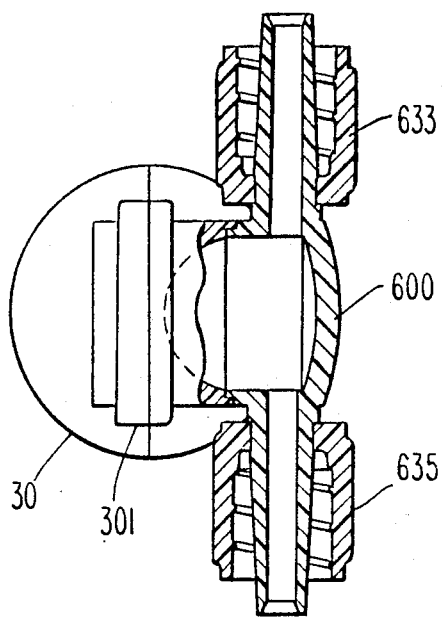
FIG. 6 is a partial vertical-sectional view of the transducer housing of a third embodiment of the present invention.

The third embodiment of the present invention, shown in FIG. 6, is generally similar to the first two embodiments but differs in not having a valve for regulating fluid flow between an inlet port 633 and an outlet port 635. Fluid flow is fixed, insofar as the transducer system is concerned, by the dimensions and characteristics of the inlet and outlet ports and the fluid flow path.

As in the embodiment of FIG. 1, the FIG. 6 embodiment includes transducer housing 301 (similar to housing 300) and mounting flange 30 mounted to curtain wall front surface 13 (not shown), behind which is located an electrical connection port (31 in FIG. 1, but not seen in FIG. 6). Housing 301 differs from housing 300 in that housing 301 includes a closure wall 600 at its rightwardly facing end (as seen in the figures) rather than being open to the fluid passageway in a flush/flow valve assembly.

It should be pointed out that the embodiment shown in FIG. 6 also may be used by closing off fluid outlet port 635 and connecting fluid inlet 633 to the leg of a "T" section coupling with saline solution flowing through the top of the "T" section coupling. In such a case, the transducer measures the static pressure built up in the line running from the "T" section coupling to fluid inlet port 633.

Figure 7:
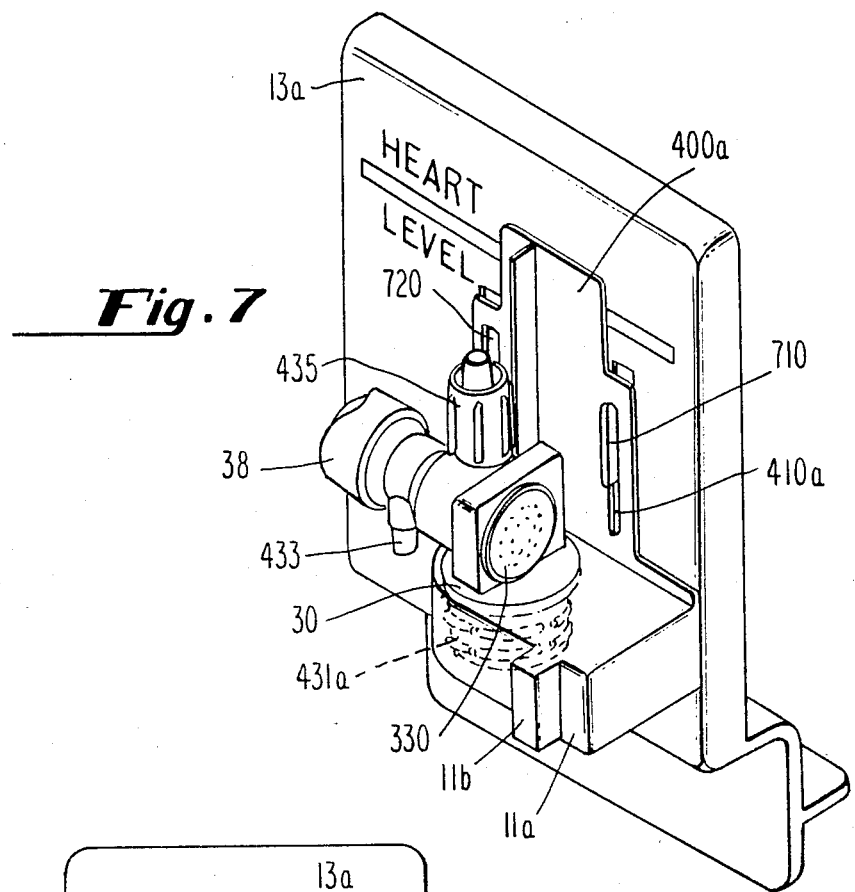
FIG. 7 is a perspective view of a fourth embodiment of the present invention.
Figure 8:
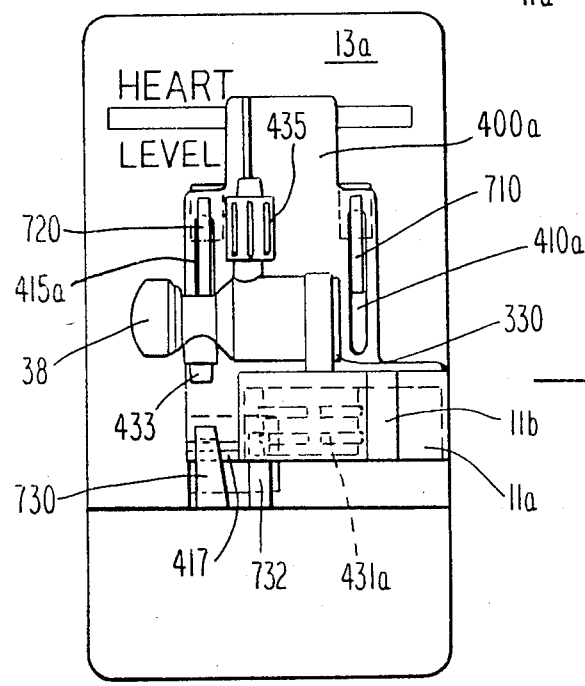
FIG. 8 is a front view of a fourth embodiment of the present invention.
Figure 9:
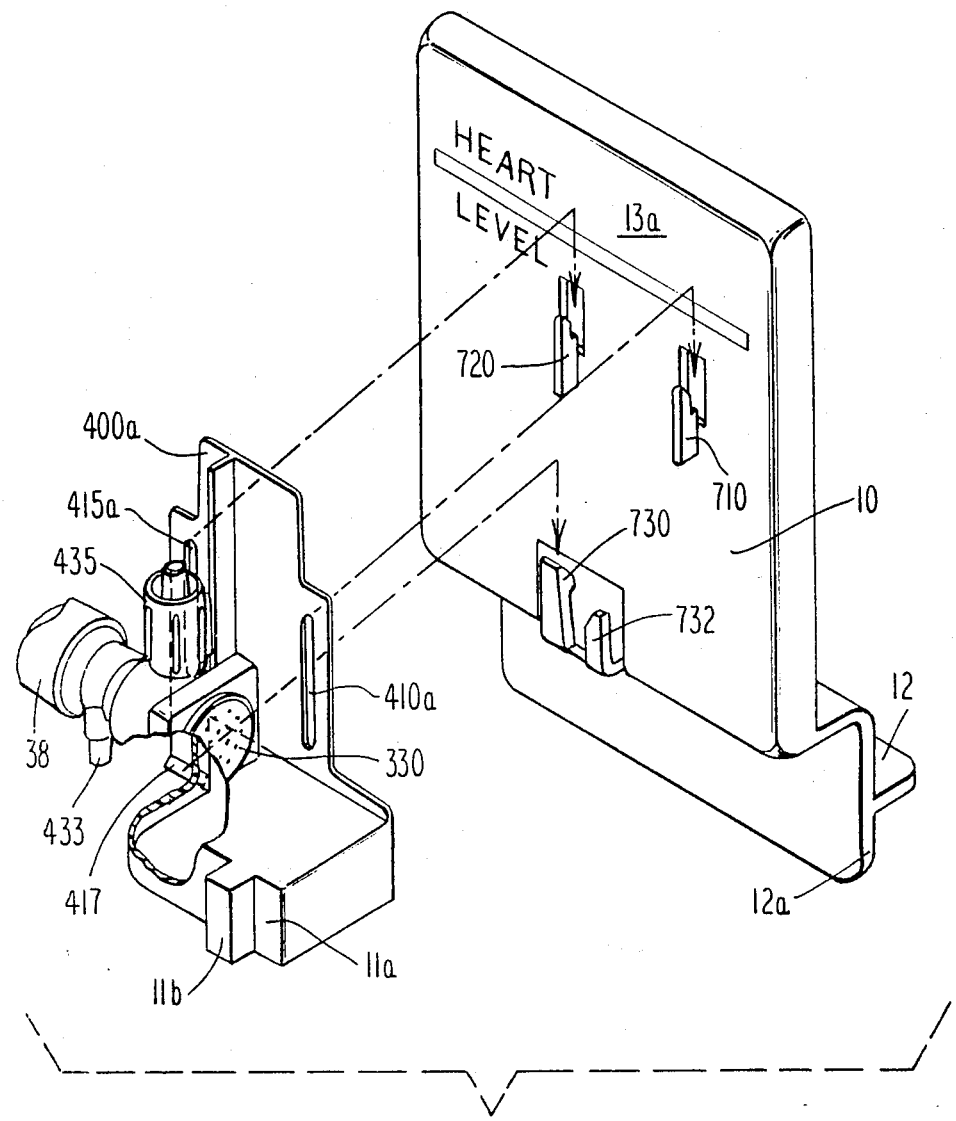
FIG. 9 is an exploded perspective view of a fourth embodiment of the present invention.

The fourth embodiment of the present invention, shown in FIGS. 7–9, is similar to the first two embodiments but differs in the configuration of the curtain wall which provides isolation of the electrical connection and inhibits fluid impingement on the electrical connection. As shown in FIGS. 7–9, curtain 10 is comprised of front surface 13a, and flanges 12 and 12a, as in embodiments described above. In addition, curtain 10 further comprises notched flanges 710, 720, and fingers 730, 732, and cooperating curtain wall 11a.

As described in connection with the embodiment of the present invention shown in FIG. 4, the transducer/flusher may be mounted on a patient-mountable base. Base 400a may be mounted either on front surface 13a of curtain 10, or with the use of retaining straps (not shown) be secured to the patient. When base 400a is mounted on curtain 10, front surface 13a provides an enclosing wall for the area around socket 431a. In the instance wherein base 400a is held in place on a patients arm by retaining straps, the surface of the patients skin provides such an enclosing wall.

In most respects, the transducer/flusher of FIGS. 7–9 is identical to those previously described. The fluid connections 433, 435, cylindrical projection 330, flange 30, and flange 38 are retained and serve similar functions to those already described.

Base 400a has slots 410a, 415a of suitable width to accept either flanges 710, 720, or a flexible strap similar to strap 500. The lower edge of base 400a is provided with a ridge 417 which engages finger 730 when base 400a is mounted on curtain wall 10. Base 400a is also provided with a projecting curtain wall 11a. Flange 30 is secured to wall 11a with electrical socket 431a (shown in phantom) on the underside of wall 11a as shown in FIGS. 7–9. Wall 11a is provided with a channel 11b which engages a portion of connector cap 25 when connector 15 is connected to socket 431a.

As may be appreciated from the Figures, curtain wall 11a provides isolation of electrical connector 431a from fluid connections 433, 435. Furthermore, curtain wall 10 may be positioned on a bedside pole prior to insertion and seating of base 400a, in order to permit better manipulation of the transducer/flusher during establishment of saline flow and electrical connection. Finally, only one configuration of the device is necessary to serve as both a patient-mounted and as a pole-mounted system.

Having described the invention with respect to certain embodiments, it should nonetheless be understood that other configurations will be apparent to those skilled in the art. It is intended therefore that this invention be defined by the claims which follow so as to encompass all of those variations within the true spirit and scope of the invention.

We claim:

1. In a pressure transducer unit for blood pressure monitoring having a housing which includes on its external surface, first and second fluid input and output ports, and an electrical connection port, said housing including a fluid flow path between said fluid ports, said electrical connection port containing a first electrical connector electrically isolated from said fluid flow path, pressure transducer means positioned in pressure sensing communication with said fluid flow path for developing a signal representative of the pressure of a fluid in said fluid flow path, means for removably connecting and disconnecting fluid input and output connections to said fluid input and output ports and means for removably connecting and disconnecting a second electrical connector to said first electrical connector within said housing, the improvement consisting of:

(a) splash curtain means for preventing movement of fluid, external to said housing, from the space surrounding said fluid input and output ports to the space surrounding said electrical connection port, wherein said splash curtain means comprises a barrier wall located on the exterior of said housing and interposed between said fluid ports and said electrical connection port, adapted for deflecting fluid, which may escape from said fluid ports, away from said electrical connection port.

2. A pressure transducer unit according to claim 1 wherein said splash curtain means includes means for attachment to a pole.

3. Splash curtain means according to claim 2 wherein said means for attachment to a pole include a vertically extending mounting flange.

4. Splash curtain means according to claim 2 wherein said means for attachment to a pole include a horizontally extending mounting flange.

5. A pressure transducer unit according to claim 1 further including a connector housing associated with said second electrical connector, said connector housing and said electrical connection port of said pressure transducer housing including fluid seal means adapted for preventing fluids from entering said electrical connection port.

6. A pressure transducer unit according to claim 5 wherein said fluid seal means includes a connector housing containing an O-ring.

7. A pressure transducer according to claim 5 wherein said fluid seal means includes a cap adapted for protecting said second electrical connector from fluid contact when said first electrical connector is disconnected from said electrical connection port of said pressure transducer housing.

* * * * *